(12) United States Patent
Katsuyoshi et al.

(10) Patent No.: US 8,986,243 B2
(45) Date of Patent: Mar. 24, 2015

(54) PERITONEAL DIALYSIS PATIENT CONNECTION SYSTEM

(75) Inventors: Sobue Katsuyoshi, Ome (JP); William R. Griswold, Bristol, WI (US); William W. Han, Long Grove, IL (US); Andrew Steinhaus, Libertyville, IL (US); Hiroshi Oishi, Tokyo (JP)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 114 days.

(21) Appl. No.: 13/421,469

(22) Filed: Mar. 15, 2012

(65) Prior Publication Data

US 2012/0209168 A1  Aug. 16, 2012

Related U.S. Application Data

(63) Continuation of application No. 11/773,623, filed on Jul. 5, 2007, now Pat. No. 8,157,761.

(51) Int. Cl.
| | |
|---|---|
| *A61M 39/18* | (2006.01) |
| *A61M 39/16* | (2006.01) |
| *A61L 2/10* | (2006.01) |
| *A61M 1/28* | (2006.01) |

(52) U.S. Cl.
CPC ............. *A61M 39/18* (2013.01); *A61M 39/165* (2013.01); *A61M 1/28* (2013.01); *A61L 2/10* (2013.01); *A61M 1/285* (2013.01)
USPC .......................................................... 604/29

(58) Field of Classification Search
CPC . A61M 5/1626; A61M 39/165; A61M 39/10; A61M 39/1011; A61M 39/14; A61M 39/20; A61M 2039/1066; A61M 2039/1033; A61M 1/28; A61J 1/14

USPC .............. 604/29, 533–538, 6.08, 199; 422/24
See application file for complete search history.

(56) References Cited

U.S. PATENT DOCUMENTS

| | | |
|---|---|---|
| 1,896,379 A | 2/1933 | Ross |
| 2,145,196 A | 1/1939 | Biggs |
| 2,249,473 A | 7/1941 | Jackson |
| 3,227,877 A | 1/1966 | Dreyfus |

(Continued)

FOREIGN PATENT DOCUMENTS

| | | |
|---|---|---|
| DE | 1936245 | 2/1971 |
| DE | 3210148 | 9/1983 |

(Continued)

OTHER PUBLICATIONS

European Office Action issued Jul. 29, 2013 for related European Appln. No. 08781255.8.

(Continued)

*Primary Examiner* — Andrew Gilbert
(74) *Attorney, Agent, or Firm* — K&L Gates LLP

(57) ABSTRACT

Peritoneal dialysis connectors, connector sets, connector systems and methods are disclosed. In an embodiment, a connector includes, a body, a spike located at a first end of the body, a sealing ring sized to seal inside a female connector and located adjacent to the spike end, threads located adjacent to the sealing ring, and at least one barbed ring located adjacent to the threads at a second end of the body. The at least one barbed ring is configured to seal the second end of the body to a tube.

31 Claims, 10 Drawing Sheets

(56) References Cited

U.S. PATENT DOCUMENTS

| | | | | |
|---|---|---|---|---|
| 3,391,951 | A | 7/1968 | Miller | |
| 3,413,097 | A | 11/1968 | Jungner | |
| 3,626,938 | A | 12/1971 | Versaci | |
| 3,709,222 | A | 1/1973 | Devries | |
| 3,780,736 | A | 12/1973 | Chen | |
| 3,814,680 | A | 6/1974 | Wood | |
| 3,840,011 | A | 10/1974 | Wright | |
| 3,916,950 | A | 11/1975 | Mongerson et al. | |
| 3,926,556 | A | 12/1975 | Boucher | |
| 3,955,922 | A | 5/1976 | Moulthrop | |
| 3,957,082 | A | 5/1976 | Fuson et al. | |
| 3,986,508 | A * | 10/1976 | Barrington | 604/411 |
| 3,994,686 | A | 11/1976 | Rauser et al. | |
| 4,056,116 | A | 11/1977 | Carter et al. | |
| 4,063,890 | A | 12/1977 | Baron | |
| 4,069,153 | A | 1/1978 | Gunther | |
| 4,080,965 | A | 3/1978 | Phillips | |
| 4,096,859 | A | 6/1978 | Agarwal et al. | |
| 4,121,107 | A | 10/1978 | Bachmann | |
| 4,139,010 | A * | 2/1979 | Dykstra | 604/263 |
| 4,141,686 | A | 2/1979 | Lewis | |
| 4,161,949 | A * | 7/1979 | Thanawalla | 604/411 |
| 4,169,474 | A | 10/1979 | Wagner | |
| 4,173,234 | A | 11/1979 | Thomas | |
| 4,196,730 | A | 4/1980 | Wilson | |
| 4,201,917 | A | 5/1980 | Graentzel | |
| 4,219,055 | A | 8/1980 | Wright | |
| 4,219,221 | A | 8/1980 | Webb | |
| 4,239,041 | A | 12/1980 | Popovich et al. | |
| 4,242,310 | A | 12/1980 | Greff et al. | |
| 4,291,701 | A | 9/1981 | Bowman | |
| 4,306,976 | A | 12/1981 | Bazzato | |
| 4,338,933 | A | 7/1982 | Bayard et al. | |
| 4,346,703 | A * | 8/1982 | Dennehey et al. | 604/406 |
| 4,387,879 | A * | 6/1983 | Tauschinski | 251/149.1 |
| 4,405,312 | A * | 9/1983 | Gross et al. | 604/29 |
| 4,405,315 | A | 9/1983 | Handt | |
| 4,412,834 | A * | 11/1983 | Kulin et al. | 604/29 |
| 4,433,244 | A * | 2/1984 | Hogan | 250/455.11 |
| 4,439,188 | A * | 3/1984 | Dennehey et al. | 604/534 |
| 4,439,193 | A * | 3/1984 | Larkin | 604/411 |
| 4,473,369 | A * | 9/1984 | Lueders et al. | 604/244 |
| 4,475,900 | A * | 10/1984 | Popovich et al. | 604/28 |
| 4,500,788 | A * | 2/1985 | Kulin et al. | 250/455.11 |
| 4,503,333 | A | 3/1985 | Kulin et al. | |
| 4,541,829 | A | 9/1985 | Munsch et al. | |
| 4,557,727 | A | 12/1985 | Handt | |
| 4,596,551 | A | 6/1986 | Golinski et al. | |
| 4,617,012 | A * | 10/1986 | Vaillancourt | 604/29 |
| 4,626,245 | A | 12/1986 | Weinstein | |
| 4,626,845 | A | 12/1986 | Ley | |
| 4,655,753 | A * | 4/1987 | Bellotti et al. | 604/534 |
| 4,655,762 | A | 4/1987 | Rogers | |
| 4,675,007 | A | 6/1987 | Terry | |
| 4,695,276 | A | 9/1987 | Shinno et al. | |
| 4,738,668 | A | 4/1988 | Bellotti et al. | |
| 4,755,292 | A | 7/1988 | Merriam | |
| 4,769,017 | A | 9/1988 | Fath et al. | |
| 4,774,415 | A | 9/1988 | Biegel et al. | |
| 4,840,621 | A | 6/1989 | Larkin et al. | |
| 4,869,286 | A | 9/1989 | Williams et al. | |
| 4,873,446 | A | 10/1989 | Kreitmair et al. | |
| 4,878,516 | A | 11/1989 | Mathieu | |
| 4,882,496 | A | 11/1989 | Bellotti et al. | |
| 4,895,570 | A * | 1/1990 | Larkin | 604/411 |
| 4,952,812 | A | 8/1990 | Miripol et al. | |
| D310,881 | S | 9/1990 | Larkin et al. | |
| 5,014,494 | A | 5/1991 | George | |
| 5,047,011 | A | 9/1991 | Caron et al. | |
| 5,053,003 | A * | 10/1991 | Dadson et al. | 604/28 |
| 5,057,074 | A | 10/1991 | Suzuki et al. | |
| 5,071,413 | A * | 12/1991 | Utterberg | 604/533 |
| 5,125,911 | A | 6/1992 | Grabenkort et al. | |
| 5,184,020 | A | 2/1993 | Hearst et al. | |
| 5,250,041 | A | 10/1993 | Folden et al. | |
| 5,279,605 | A | 1/1994 | Karrasch et al. | |
| 5,311,899 | A | 5/1994 | Isayama et al. | |
| 5,334,139 | A | 8/1994 | Jeppsson et al. | |
| 5,350,357 | A * | 9/1994 | Kamen et al. | 604/29 |
| 5,399,156 | A | 3/1995 | Lindsay | |
| 5,472,720 | A | 12/1995 | Rakhimov et al. | |
| 5,540,265 | A | 7/1996 | Polaschegg et al. | |
| 5,542,913 | A | 8/1996 | Lindsay | |
| 5,572,992 | A | 11/1996 | Kankkunen et al. | |
| 5,583,948 | A | 12/1996 | Shibayama | |
| 5,611,506 | A * | 3/1997 | Berger et al. | 248/65 |
| 5,612,001 | A | 3/1997 | Matschke | |
| 5,637,267 | A * | 6/1997 | Lo et al. | 264/80 |
| 5,647,984 | A | 7/1997 | Hovland et al. | |
| 5,707,911 | A | 1/1998 | Rakhimov et al. | |
| 5,714,119 | A | 2/1998 | Kawagoe et al. | |
| 5,733,457 | A | 3/1998 | Hovland et al. | |
| 5,743,892 | A * | 4/1998 | Loh et al. | 604/537 |
| 5,792,419 | A | 8/1998 | Williamson et al. | |
| 5,810,398 | A * | 9/1998 | Matkovich | 285/3 |
| 5,843,379 | A | 12/1998 | Kristensen | |
| 5,900,211 | A | 5/1999 | Dunn et al. | |
| 5,925,014 | A | 7/1999 | Teeple Jr. | |
| 5,948,247 | A | 9/1999 | Gillerfalk et al. | |
| 5,971,972 | A * | 10/1999 | Rosenbaum | 604/411 |
| 6,013,918 | A | 1/2000 | Bushnell et al. | |
| 6,096,011 | A * | 8/2000 | Trombley et al. | 604/256 |
| 6,146,600 | A | 11/2000 | Williamson | |
| 6,171,561 | B1 | 1/2001 | Williamson et al. | |
| 6,228,332 | B1 | 5/2001 | Dunn et al. | |
| 6,234,538 | B1 | 5/2001 | Lauer | |
| 6,245,570 | B1 | 6/2001 | Grimm et al. | |
| 6,293,921 | B1 * | 9/2001 | Shinmoto et al. | 604/29 |
| 6,440,095 | B1 | 8/2002 | Utterberg | |
| 6,443,147 | B1 | 9/2002 | Matter | |
| 6,461,568 | B1 | 10/2002 | Eckhardt | |
| 6,468,424 | B1 | 10/2002 | Donig et al. | |
| 6,565,525 | B1 | 5/2003 | Burbank et al. | |
| 6,565,803 | B1 | 5/2003 | Bolton et al. | |
| 6,696,023 | B2 | 2/2004 | Grimm et al. | |
| 6,730,113 | B2 | 5/2004 | Eckhardt et al. | |
| 6,736,797 | B1 | 5/2004 | Larsen et al. | |
| 6,814,726 | B1 | 11/2004 | Lauer | |
| 6,911,025 | B2 | 6/2005 | Miyahara | |
| 7,083,605 | B2 | 8/2006 | Miyahara | |
| 7,195,615 | B2 | 3/2007 | Tan | |
| 7,232,429 | B2 | 6/2007 | Moreci | |
| 7,306,197 | B2 | 12/2007 | Parrino et al. | |
| 7,727,220 | B2 * | 6/2010 | Wieslander et al. | 604/411 |
| 2008/0015493 | A1 * | 1/2008 | Childers et al. | 604/29 |

FOREIGN PATENT DOCUMENTS

| EP | 0311848 | 4/1989 |
| EP | 0507321 | 10/1992 |
| EP | 0575970 | 12/1993 |
| EP | 0704227 | 4/1996 |
| JP | 2001-238945 | 9/2001 |
| WO | 8604674 | 8/1986 |
| WO | 92/11046 | 7/1992 |
| WO | 96/25214 | 8/1996 |

OTHER PUBLICATIONS

Written Opinion of the International Searching Authority for International Application No. PCT/US2008/068956 mailed Jan. 19, 2009.
Japanese Office Action issued Jan. 22, 2013 for corresponding Japanese Appln. No. 2010-515243.
European Office Action issued Sep. 15, 2014 for related European Appln. No. 08781255.8.

* cited by examiner

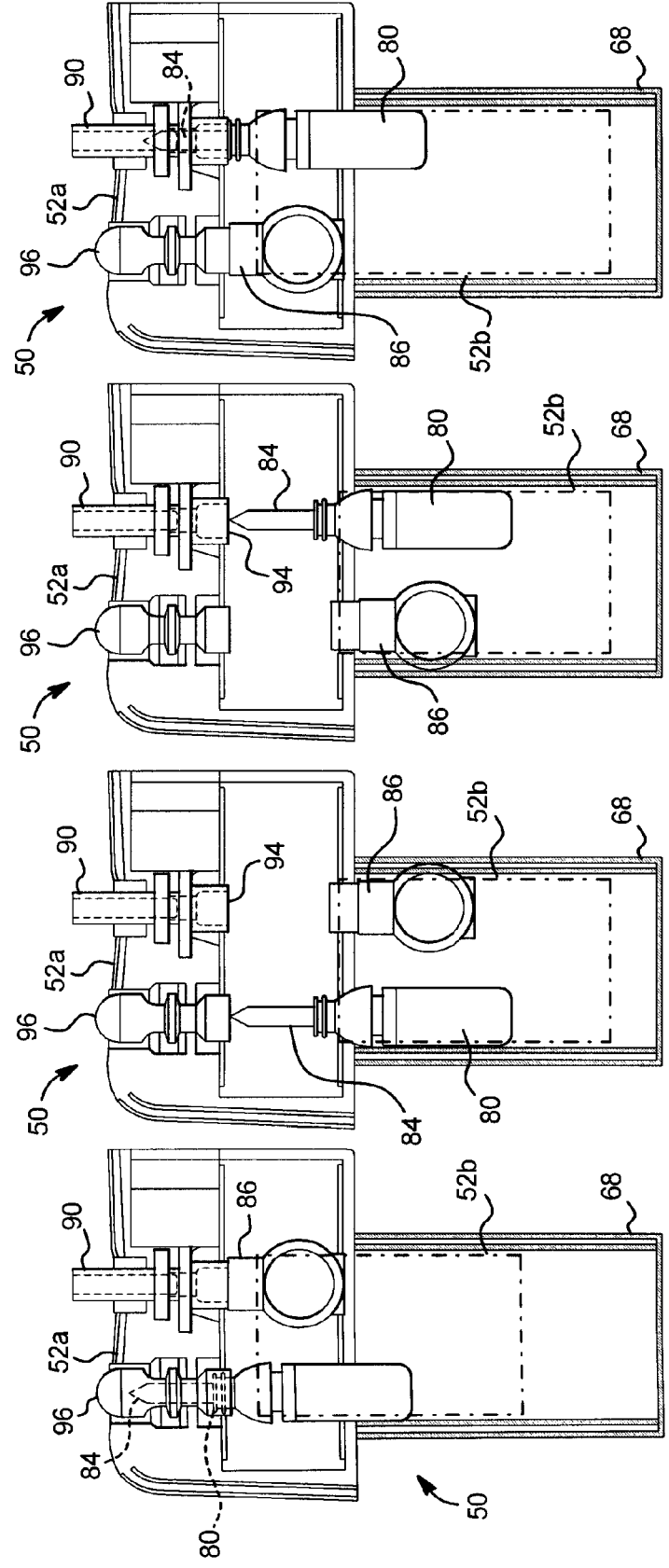

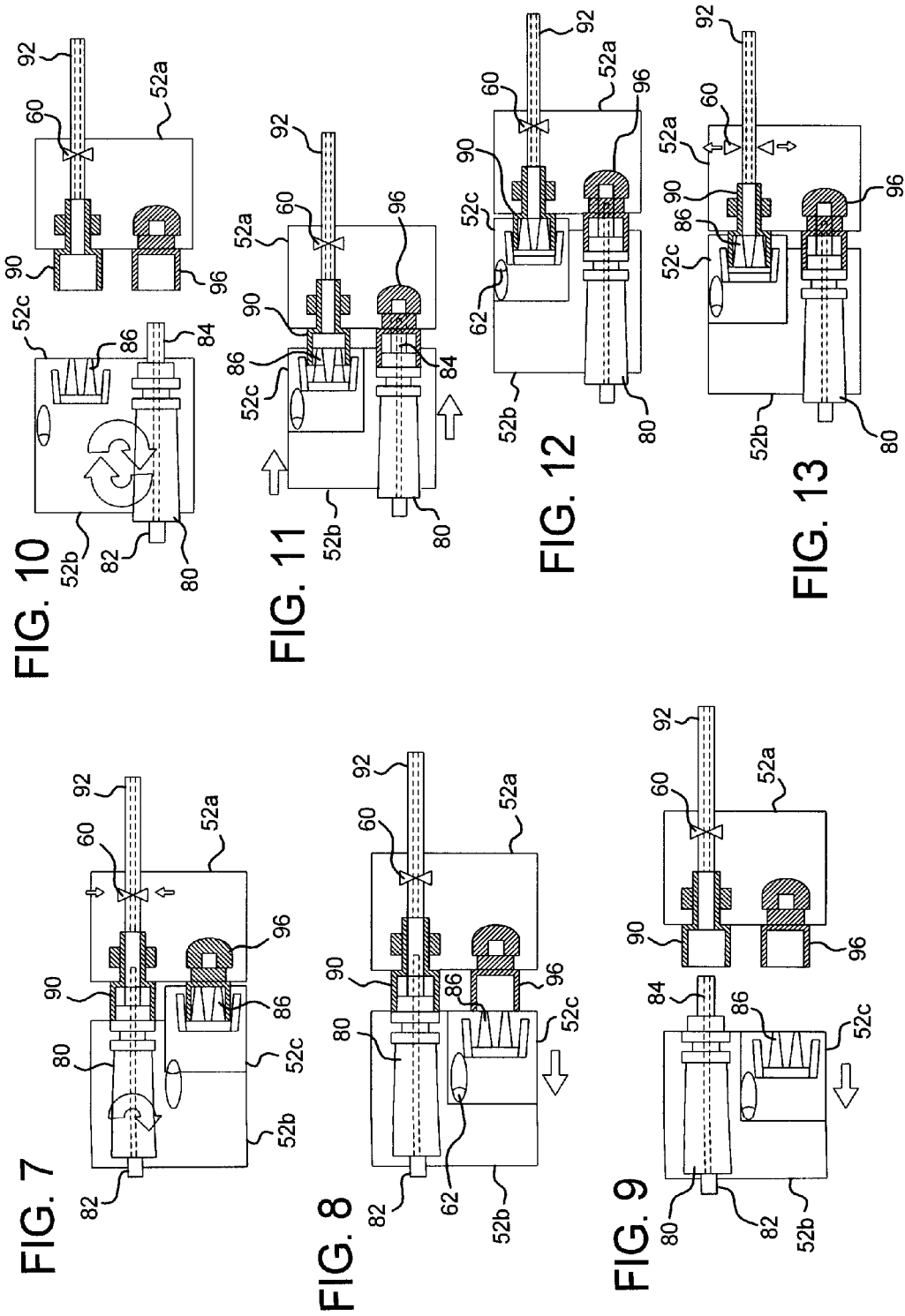

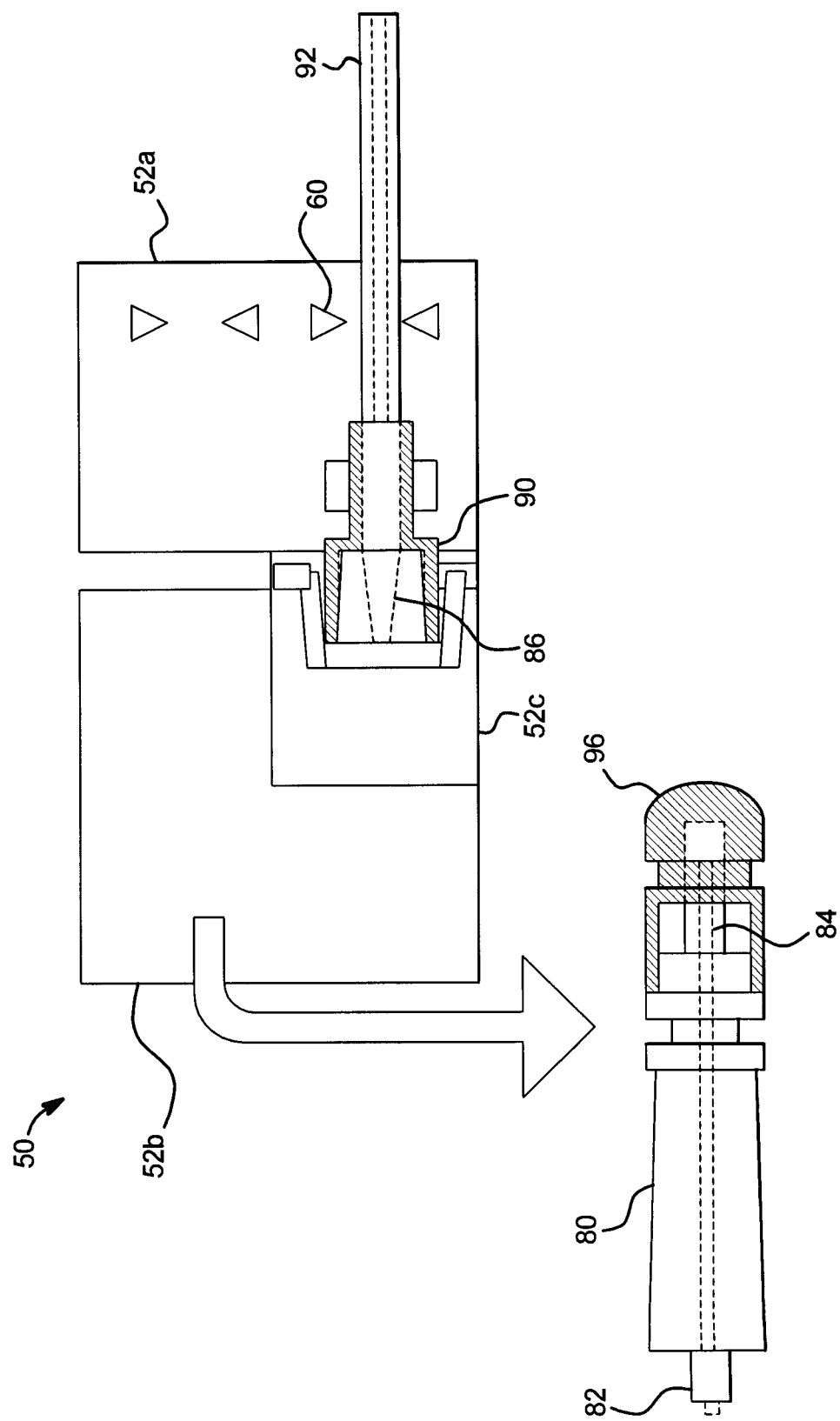

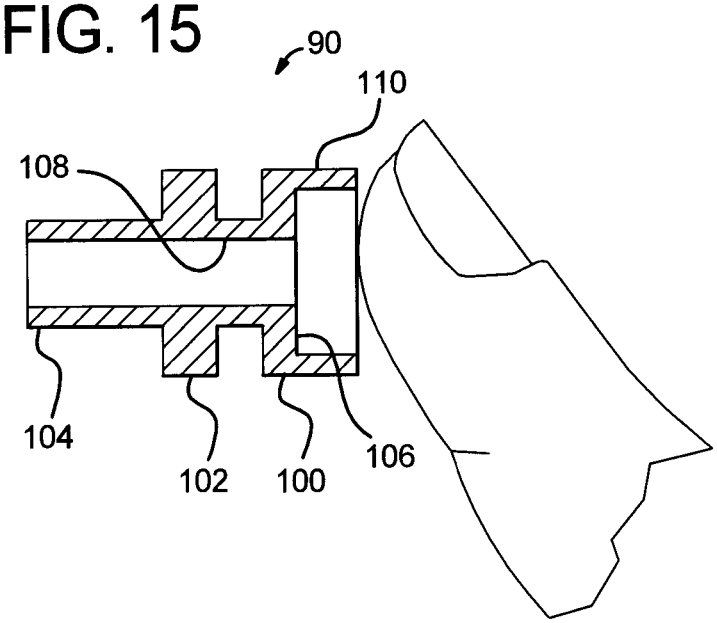
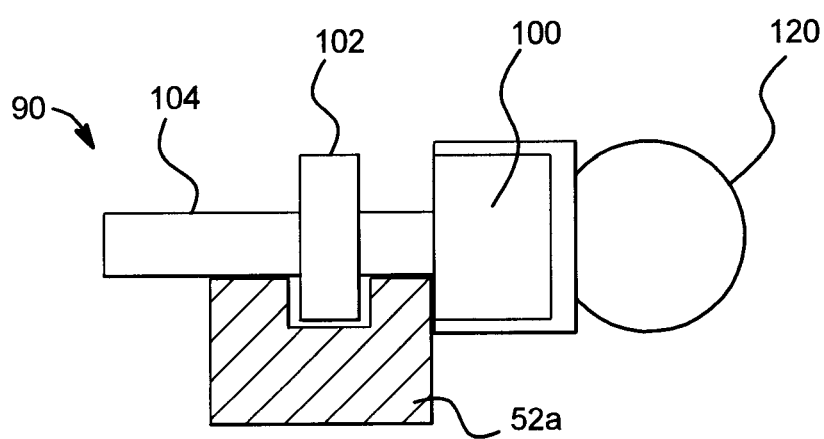

PERITONEAL DIALYSIS PATIENT CONNECTION SYSTEM

PRIORITY CLAIM

This application claims priority to and the benefit as a continuation application of U.S. Patent Application entitled, "Peritoneal Dialysis Patient Connection System", Ser. No. 11/773,623, filed Jul. 5, 2007, now abandoned, the entire contents of which are incorporated herein by reference and relied upon.

BACKGROUND

The present disclosure relates generally to medical device connectors and more specifically to patient connectors for peritoneal dialysis.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

One type of kidney failure therapy is peritoneal dialysis, which uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD").

The technique of CAPD to remove impurities from the blood of a patient whose kidneys have failed permits the patient being dialyzed to carry a surgically implanted catheter, which is generally connected (intermittently) to a peritoneal dialysis transfer set. For CAPD treatment, the transfer set, in turn, is connected to a bag of peritoneal dialysis solution, which is emptied through the transfer set into the peritoneal cavity (CAPD infusion phase). For CAPD, the patient is not "tied" to a machine and can be ambulatory while the dialysis across the peritoneal membrane (CAPD dwell phase) occurs. After the dwell phase, the peritoneal dialysis solution is drained (CAPD drain phase) from the peritoneal cavity. This can be done by allowing the solution to flow back into the supply bag; there is preferably no disconnection of the bag during the dwell phase. After the drain phase, the bag with spent peritoneal dialysis solution may be disconnected from the transfer set and discarded.

Automated peritoneal dialysis ("APD") is similar to CAPD in that the dialysis treatment includes drain, fill, and dwell cycles. APD machines or "cyclers", however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during dialysate. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

All of the above systems require the patient to connect the patient's indwelling catheter to a PD supply apparatus via a transfer set. The patient connection must be kept sterile or the patient can suffer from a condition called peritonitis. The patient connection should also be easy for the patient to make and unmake because the patient is usually performing these tasks at home and/or alone. Accordingly, a need exists for improved peritoneal dialysis patient connection systems.

SUMMARY

The present disclosure includes an improved patient connector or patient assist system for medical fluid systems including peritoneal dialysis ("PD"). In particular, the connectors and connections relate to patient connectors and connections for any type of PD, such as automated peritoneal dialysis ("APD") and continuous ambulatory peritoneal dialysis ("CAPD"). The patient connection system generally includes a patient transfer set having a spine connector. A female or port connector of a bag supply line ("CAPD") or cycler patient line ("APD") connects to the spike connector of the patient's transfer set. The female and spike connectors are positioned in a connection mechanism, which is described below as being a rotating drum type of mechanism. The rotating drum mechanism is in turn placed moveably within a housing having ultraviolet light ("UV") applicator positioned to sterilized connectors loaded into the drain mechanism.

The housing in one embodiment includes a lid connected hingedly to a lower portion of the housing. Half of the drain device is fitted to and latches with the lid. The other half is fitted into the lower portion. The device halves can then be separated to load and unload the connectors and plugs. The UV applicator is also split into the lid and lower portion and embedded so to be positioned on the outsides of the drain device when load into the lid and lower portion of the housing.

The rotational drum connection/disconnection device includes three main components, namely: (i) a female or port holder; (ii) a transfer set holder; and (iii) a slide holder. The port holder is fixed inside of housing, such as one also holding a light applicator housing, which radiates light onto the connectors placed into the drum connection/disconnection device as described in detail below. The port holder in one embodiment holds a female or port connector (connected to a solution line, e.g., from a supply bag directly or from a cycler) and a female plug.

The transfer set holder holds a spike or patient connector and rotates and translates relative to the port holder and holds the patient's transfer set spike connector (connected to patient's indwelling catheter). The transfer set holder in one embodiment includes and slidingly engages a slide holder, which translates back and forth relative to the remainder of the transfer set holder and the port holder.

The slide holder can be part of or separate from the transfer set holder. The slide holder in one embodiment holds a male plug. In one embodiment there are two relative translating movements, (i) the slide holder relative to the remainder of the transfer set holder and the port holder and (ii) the transfer set holder as a whole (including the slide holder) relative to the port holder. In another embodiment, the slide holder is not provided with the transfer set holder such that there is only one translational movement, namely, the transfer set holder as a whole (including the patient connector and male plug) relative to the port holder.

When the transfer set holder is rotated relative to the port holder, the slide holder (holding the male plug) rotates with the remainder of the transfer set holder (holding the male spike connector). This motion allows the transfer set holder to flip-flop back and forth between aligning the connectors with each other (connected for treatment) or with a mating plug (disconnected for, e.g., dwell, end of treatment or temporary disconnect).

One connection sequence for the above-described patient assist device operates as follows, wherein the device includes a first portion configured to hold a fluid supply connector and a first plug; a second portion configured to hold a patient connector and a second plug; an ultraviolet light ("UV") applicator; and wherein the first and second portions cooperate with the UV applicator so that: (i) the first plug initially plugs the patient connector and the second plug initially plugs the supply connector, (ii) the first and second portions are translated away from each other via at least one translation mechanism, unplugging the first and second plugs from the patient connector and the supply connector, respectively, (iii) the first and second portions are rotated with respect to each other, (iv) the UV applicator irradiates at least a portion of the fluid supply and patient connectors; and (v) the first and second portions are translated towards each other via the at least one translation mechanism, connecting the patient connector to the supply connector and the first plug to the second plug.

One disconnection sequence for the above-described patient assist device operates as follows: (i) the first plug is connected initially to the second plug and the patient connector is connected initially to the supply connector, (ii) the first and second portions are translated away from each other via at least one translation mechanism, disconnecting the first plug from the second plug and the patient connector from the supply connector, (iii) the first and second portions are rotated with respect to each other, (iv) the UV applicator irradiates at least a portion of the patient connector and the supply connector, and (v) the first and second portions are translated with respect to each other via the at least one translation mechanism, connecting the first plug to the patient connector and the second plug to the supply connector.

The female or port connector mounted in the port holder of the above-described patient assist connection device has a frangible seal that is manually broken to expose a diaphragm, which prevents flow through the connector. The spike connector includes a spike or piercing end that pierces the diaphragm and inserts into the female connector. The spike can have a cut-away portion at its sharpened end, with the sharpened end defining a pointed edge at one side of the spike opposite the cut-away portion. Such structure results in diaphragm not being cut away from the interior wall of the female connector, so that the diaphragm remains attached to the interior wall of the connector. This prevents the diaphragm passing through the tubular system into the peritoneal cavity of the patient, or falling free to block flow at some point in the system.

If desired, the female and spike connectors can be partially or substantially opaque to ultraviolet ("UV") light if this results in the connectors being made of a less expensive material, and if the interior portions of the connectors are sterilized at the factory. Here, only exterior portions of the connectors have to receive the antimicrobial effects of the UV as described herein. Alternatively, the spike connectors can be made of a UV transmissive material and be sterilized inside and outside upon connection and disconnection (as highlighted above), for example, in addition to being sterilized at the factory.

The female or port connector as shown below in one embodiment includes a shroud that tends to prevent the portion of the female connector that interfaces with the spike connector from patient touch during connection and disconnection. The spike connector also includes a sealing portion, e.g., one or more o-ring type annular projection that seals to the inner wall of the shroud. The shroud therefore also serves to prevent the patient from touching the sealing portion after connection. This tends to prevent contamination from entering the female connector upon disconnecting the female and spike connectors. The shroud further serves to prevent overadvancement of the spike connector within the female connector.

The shroud and the rotational drum connection/disconnection device are configured such that the shroud of the female connector extends past the port holder of the connection/disconnection device. This allows the female connector to be inserted into the port connector of the rotational drum connection/disconnection device prior to removing a tip protector from an end of the female connector. The tip protector protects the shroud end of the female connector until time for use. Here, the patient can hold the rotational drum connection/disconnection device and pull the tip connector off without having to touch the female connector. This further prevents the female connector from becoming contaminated in the first place and lessens the load on the UV light applicator.

An additional advantage of the shroud is that the spike end of the mating patient connector is not contaminated when the patient removes the patient connector and associated spike from the shrouded end of the female supply connector. Such contamination is a common occurrence with known connectors.

The spike connector and the female or port connector as discussed above are each connected to a tube on the opposite end from the end at which the spike connector mates with the female connector. In one embodiment, as discussed above, the spike connector is connected to a tube that connects to or is part of the patient's transfer set and that communicates with the patient's indwelling catheter. The female or port connector connects to a tube that communicates with a fluid supply, either directly (CAPD) or via a disposable cassette operable with a cycler (APD). In one embodiment, one or both of the spike connector and the female connector includes at least one barbed ring configured to seal the tube to the connector.

The barbed ring is tapered such that it is relatively easy to insert the tube over the at least one barbed ring but relatively difficult to remove the tube, making a good, sealed connection. The at least one barbed ring is relatively easy and inexpensive to manufacture and control.

In another embodiment, the spike connector and port connector provide a snap-connection. The supply or port connector includes an undercut geometry, which mates with an annular ring of the spike connector to provide connection retention. The snap-fit is configured such that the disconnection device can readily overcome the snap-fitting force to decouple the spike connector from the female or port connector. The patient is also able to readily decouple the connectors by hand.

The snap-fit enables the connection of the spike connector to the supply connector to not have to rely on a friction fit between the spike and an inner diameter of the supply connector. The spike connector includes a spike having a stepped-down (diameter) tip, which reduces friction between the connectors and thus insertion and removal forces caused by the mating connectors.

It is accordingly an advantage of the present disclosure to provide an improved patient assist system for peritoneal dialysis ("PD").

It is another advantage of the present disclosure to provide a patient assist system operable with continuous ambulatory peritoneal dialysis ("CAPD") and automated peritoneal dialysis ("APD").

It is yet a further advantage of the present disclosure to provide a patient assist system having an improved connector connection and disconnection device.

It is still a further advantage of the present disclosure to provide an improved connector connection and disconnection device, which includes rotating and translating portions.

It is still another advantage of the present disclosure to provide an improved female or port connector having a shroud that tends to protect sensitive areas of the connector from human touch and possible contamination.

Moreover, it is an advantage of the present disclosure to provide a connector and connection and disconnection device that enables the connectors to be placed in the device prior to removing a tip protector from the connectors, further protecting sensitive areas of the connector from human touch and possible contamination.

Still another advantage of the present disclosure is to provide a connector having at least one barbed ring for connecting sealingly to a tube or conduit.

Another advantage of the present disclosure is to provide a snap-fitting connection between spike and port connector.

A further advantage of the present disclosure is to reduce insertion and removal forces for the spike and port corrector connection and disconnection.

Additional features and advantages are described herein, and will be apparent from, the following Detailed Description and the figures.

BRIEF DESCRIPTION OF THE FIGURES

FIGS. 3 to 6 further illustrate one embodiment of the rotational drum connection/disconnection and a connection sequence using the rotational drum.

FIGS. 7 to 13 are schematic views of a disconnection sequence for the rotational drum connection/disconnection.

FIG. 14 is a schematic view of a temporary disconnection/reconnection sequence for one embodiment at the rotational drum connection/disconnection device.

FIGS. 15 and 16 are sectioned elevation views illustrating a connector having a shroud tending to protect sensitive areas of the connector from human touch and possible contamination.

FIG. 17 is a sectioned elevation view illustrating a connector and holder combination providing an improved tip protector removal sequence, which tends to protect sensitive areas of the connector from human touch and possible contamination.

DETAILED DESCRIPTION

Drum Disconnection and Reconnection Device

The apparatuses and methods discussed herein are is illustrated in use with a peritoneal dialysis system, such as continuous ambulatory peritoneal dialysis ("CAPD") or an automated peritoneal dialysis ("APD"). It should be appreciated however that the teachings associated with the appended drawings are applicable to many types of medical fluid systems. In CAPD and APD, the patient connects a supply line running to either a supply bag directly (CAPD) or to a disposable cassette (APD) operable with a pumping cycler. It is important that such connection be made in a sterile manner. It is also desirable to have a convenient system for the patient, who may otherwise be ill or elderly, to operate.

The patient connects the supply line to a patient line, which can be part of a PD transfer set, which is in turn connected to a catheter dwelling within the patient's peritoneum. The patient in CAPD then connects the patient line to a drain bag to enable spent dialysate to be removed from the patient's peritoneum. The patient may have to connect multiple supply lines, each running from a separate supply bag, to the patient line. Between each supply bag for CAPD, the patient has to connect to a drain bag. Here, it is important that the patient be able to disconnect an old supply line, correct a drain line and then connect a new supply line readily and in a sterile environment.

It is also possible in CAPD and APD that the patient needs to disconnect from a supply bag or a drain bag during a fill or drain. In both procedures, therefore, it is desirable to have a convenient and sterile way for the patient to disconnect temporarily from the supply or drain connector and then to reconnect to the connector at a later time.

The apparatuses and methods provide an improved connection/disconnection device. The connectors being connected are also configured to prohibit the connectors from becoming contaminated in the first place. Still further, (i) a connector to tube connection, and (ii) connector to connector connection sequenced, and (iii) a connector to connector disconnection sequence are improved.

Figure 1:
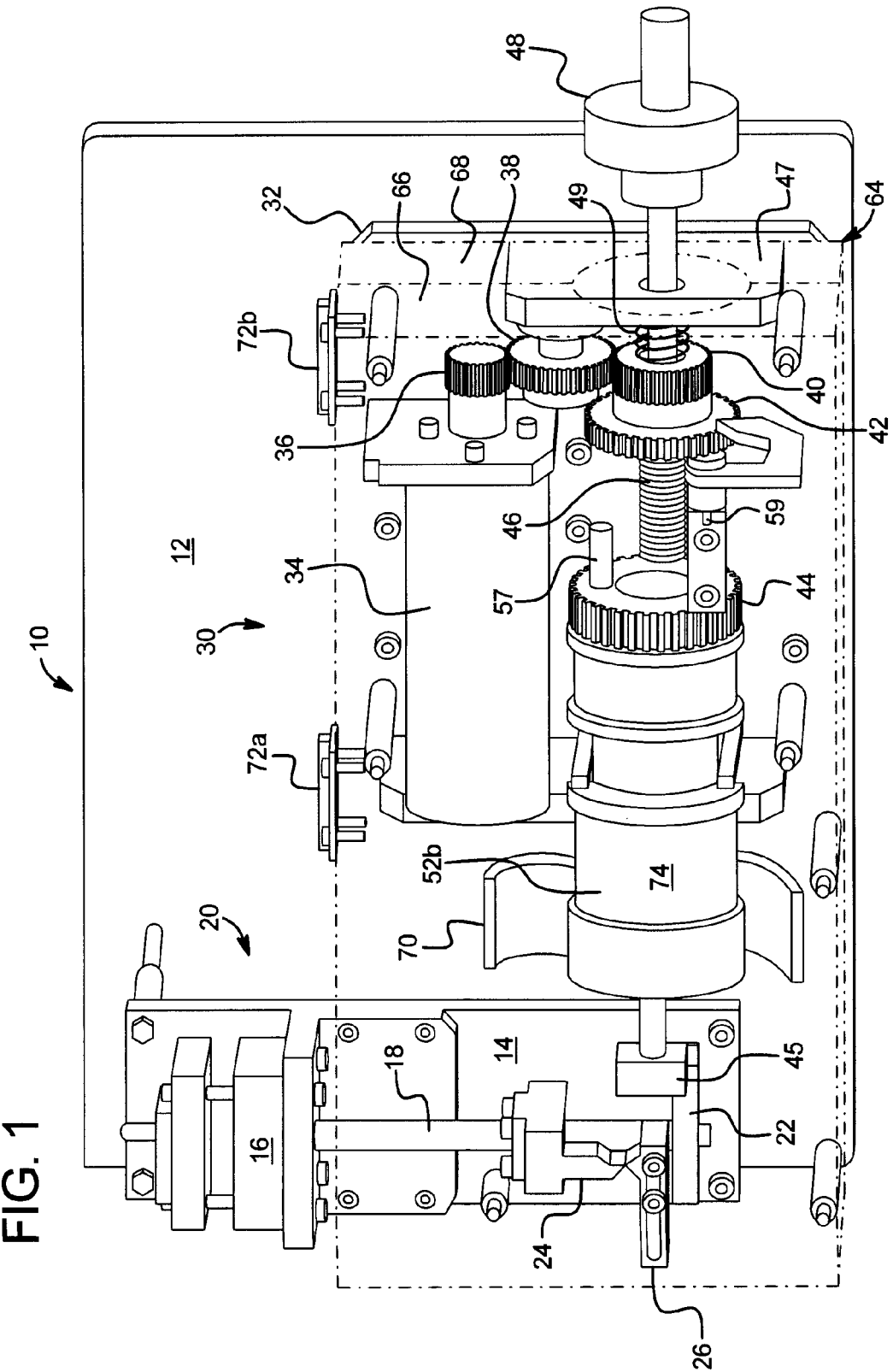
FIG. 1 is a top plan view of one embodiment of a rotational drum connection/disconnection device

Referring now to the drawings and in particular to FIG. 1, system 10 illustrates one embodiment for a sterilized rotational/translational connection/disconnection system of the present disclosure. System 10 includes a base 12 onto which occlusion subassembly 20 and a drum rotation subassembly 30 are mounted. Occlusion subassembly 20 includes an occlusion subassembly base 14, which is bolted to (e.g., set apart from) system subassembly 12. Occlusion subassembly base 14 supports an occlusion motor 16 coupled to an at least partially threaded shaft 18. A pillow block 22 supports shaft 18 at its distal end.

A translating occluder 24 is threaded onto shaft 18 and is guided on one or two sides so that it cannot rotate when shaft 18 is rotated. Instead, the guides cause translating occluder 24 to translate back and forth when shaft 18 is rotated. In this manner, translating occluder 24 translates towards or away from a stationary occluder 26 to pinch or open a line, respectively, automatically. In one embodiment, the line that is occluded is a supply line running to a supply connector 90, which is loaded into the drum rotation subassembly 30.

Drum rotation subassembly 30 includes a drum rotation subassembly base 32, which is bolted to system subassembly 12. Drum rotation subassembly base 32 supports a drum rotation motor 34 coupled to a first gear 36. First gear 36 drives a second gear 38, which through reduction increases the torque output and positionability of drum rotation motor 34. Drum rotation motor 34 can be a stepper motor, which is inherently accurately positionable. Alternatively, drum rotation motor 34 is an AC or DC bidirectional motor that operates with position sensors monitoring the rotational position of the moveable portion 52b of drum connection/disconnection device 50 (discussed in detail below). The sensors tell a controller of motor 34 when the motor should stop spinning in a particular direction.

Second gear 38 drives a third gear 40, which is roughly in a one-to-one ratio with second gear 38. Third gear 40 is coupled to fourth gear 42. Fourth gear 42 is configured to mate with a drum gear 44 located at the end of drum connection/disconnection device 52b when device 52b and gear 44 are translated over fourth gear 42.

Drum rotation subassembly 30 includes a ball screw 46, which is at least partially threaded. First and second pillow blocks 45 and 47 support either end of ball screw 46. Ball screw 46 runs underneath drum connection/disconnection device 52b as illustrated and is threaded into a block (e.g., located underneath device 52b) connected to device 52b. The threaded block is guided on one or two sides so that it cannot rotate when ball screw 46 is rotated. Instead, the guide(s) cause the block and moveable device 52b to translate back and forth when ball screw 46 is rotated. In this manner, the transfer set holder 52b translates towards or away from a stationary portion of device 50 (not shown here but described in detail below) to disconnect and reconnect connectors as discussed in detail below, automatically.

Motor 34, gears 36, 38 and 40 all drive ball screw 46 and thus the moveable port 52b of drum connection/disconnection device 50 in two directions. Gear 42 is a one-way clutch. That is, gear 42 turns drum gear 44 when gears 36, 38 and 40 are turned so that gear 42 is turned in a first, e.g., clockwise, direction when viewed from hand crank 48. However, gear 42 spins freely and does not turn drum gear 44 when gears 36, 38 and 40 are turned so that gear 42 would be turned in a second, e.g., counterclockwise, direction when viewed from hand crank 48. A spring 49 absorbs a shock from drum 50 when gear 44 of drum 50 engages gear 42. Ball screw 46 in the illustrated embodiment can also be driven manually via crank 48.

Motor 34 (or manual input) and gears 36, 38 and 40 turn ball screw 46 in one direction to pull moveable portion 52b of drum connection/disconnection device 50 away from the stationary portion (shown below as port holder 52a) of device 50 until drum gear 44 comes into operable engagement with fourth free-wheel clutch gear 42. Once such engagement begins, gear 42 begins to turn drum gear 44 and the moveable portion 52b of device 50 rotationally about its axis. That is, when motor 34 (or manual input) and gears 36, 38 and 40 are turned such that drum gear 44 and the moveable part 52b of device 50 are moving towards gear 42, gear 42 can clutch drum gear 44 and turn it, turning the moveable part 52b of connection device 50. Eventually, a stop 57 extending from gear 44 engages a stop 59 fixed to the sub-assembly base 32. Stops 57 and 59 ensure that drum gear 44 and the moveable part 52b of connection device 50 rotate a desired one-hundred-eighty degrees. Stops 57 and 59 also cause motor 34 to draw additional current, which can be sensed and serve as a trigger to stop motor 34 from turning in the direction that causes ball screw 46 to move drum gear 44 and the moveable part 52b towards stop 59

Next, motor 34 (or manual input) and gears 36, 38 and 40 turn ball screw 46 in the opposite direction to translate moveable portion 52b of drum connection/disconnection device 50 towards the stationary portion of device 50 (not illustrated in FIG. 1) until the various connectors and caps mate as shown below. When the drive train is rotating in this state, gear 42 slips against a hub extending from gear 40, such that gear 42 does not turn drum gear 44 and the moveable portion of drum 52b rotationally. That is, when motor 34 (or manual input) and gears 36, 38 and 40 are turned such that drum gear 44 and the moveable part 52b of device 50 are moving away from gear 42, gear 42 does not clutch drum gear 44 and does not turn the gear or the moveable part 52b of device 50. Eventually, a connector and cap loaded into moveable part 52b mate with a connector and cap (or vice versa) of stationary part 52a, signaling the end of travel in the connection direction.

Drum subassembly base 32 also supports an ultraviolet ("UV") light applicator 70, which is positioned around a the connector mating portion of rotational/translational connection/disconnection device 50. UV light applicator 70 irradiates the connectors loaded into device 50 during connection and disconnection. As discussed below, UV light applicator 70 can be energized when transfer set holder 52b of connection/disconnection device 50 is being rotated in one embodiment. In one embodiment, light applicator 70 is a "UV-Flash"™ applicator provided by the eventual assignee of the present application, which is described U.S. Pat. Nos. 4,412,834 and 4,503,333, owned by the eventual assignee of the present application, the entire contents of both of which are incorporated herein expressly by reference. Another suitable light applicator 70 is disclosed in copending U.S. patent application Ser. No. 11/773,824, filed Jul. 5, 2007, entitled "Peritoneal Dialysis Patient Connection System Using Ultraviolet Light Emitting Diodes", assigned to the eventual assignee of the present application, the entire contents of which are incorporated herein by reference.

Connection/disconnection system 10 includes a housing 64 having a lid 66, which is connected hingedly to a lower portion 68 of the housing via first and second hinges 72a and 72b. Housing 64 can be plastic, such as a clear plastic, and should be opaque to UV light. As shown in more detail below, in one embodiment, an upper portion 74 of the moveable portion 52b of connection/disconnection device 50 is connected to lid 66. An upper part of port holder 52a (shown below) of device 50 is fixed to and rotatable with lid 66. Upper portion 74 of transfer set holder 52b is rotatably and translatably fixed to and rotatable with lid 66.

An upper portion of light applicator 70 is fixed to and rotatable with lid 66 of housing 64. A lower portion of light applicator 70 is fixed to lower portion 68 of housing 64. In this manner, light applicator 70 is openable and closeable about connection/disconnection device 50, which is loaded into housing 64, a portion 52c of which is thereafter translatable and rotatable via lead screw 46 and gears 36, 38, 40, 42 and 44, respectively, as discussed above.

Figure 2:
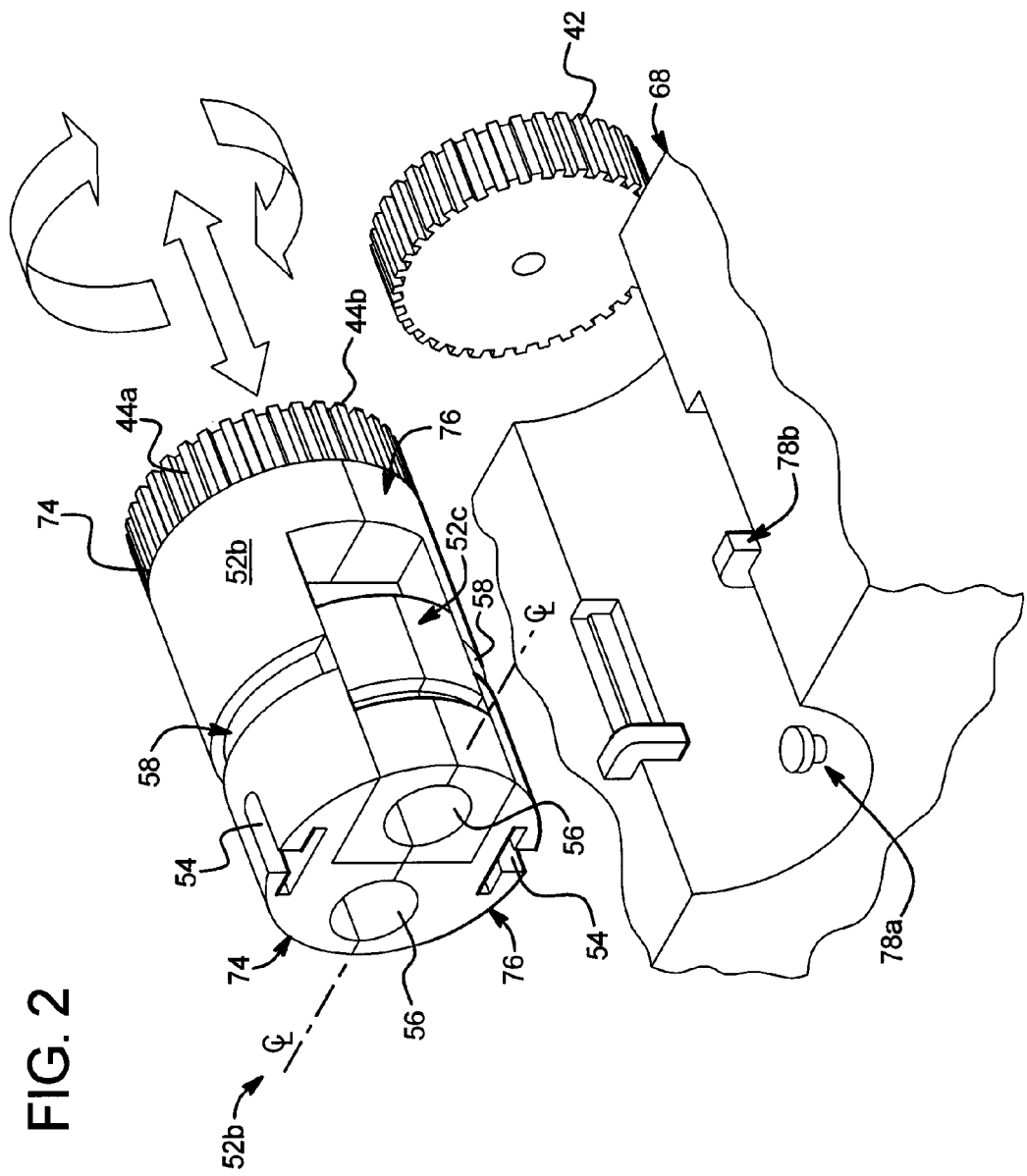
FIG. 2 illustrates a perspective view of the rotational drum connection/disconnection device of the system of FIG. 1, which employs a supply line connector portion fixed to a housing and a patient line connector portion that translates and rotates with respect to the supply line connector portion.

FIG. 2 illustrates one embodiment for the transfer set holder 52b of rotational/translational connection/disconnection device 50. As shown below, device 50 has three primary components, namely, a port holder 52a, a transfer set holder 52b and an optional slide holder 52c. Each of these parts can but does not have to be made of a UV transmissive material such as poly(trifluorochloroethane), for example sold as KEL-F™ by Minnesota Mining & Manufacturing, or other stable fluorocarbon, for example. Quartz glass, silicone rubber, appropriately stabilized hydrocarbon resin or other resins may be used as well.

In FIG. 1 above, transfer set holder 52b is illustrated. Port holder 52a is located to the left of transfer set holder 52b, i.e., above pillow block 45. Port holder 52a is not illustrated in FIG. 1, so that occluder sub-assembly 20 and the driving mechanism for transfer set holder 52b can be illustrated more completely. Port holder 52a is however illustrated in detail in the following drawings.

In FIG. 2, transfer set holder 52b is divided into upper half 74 and lower half 76, as discussed above, along centerline $C_L$. Lower half 76 of transfer set holder 52b includes a slotted groove 54 that slides over and secures to a peg or post 78a extending from or connected to a holding well of sub-assembly 30 of system 10 for of lower portion 68 of housing 64. A similar peg or post 78a extends downwardly from a holding well of lid 66 of housing 64. Upper half 74 of transfer set holder 52b of device 50 also includes a slotted groove 54 that slides over and secures to the upper peg or post 78a. As discussed above, upper and lower parts 74 and 76 of transfer set holder 52b along centerline $C_L$ are fixed to and rotatably openable with upper lid 66 and lower portion 68 of housing 64. Transfer set holder 52b includes or defines apertures 56, split along centerline $C_L$, for accepting and securing a patient connector 80 and a male plug 86 shown below in FIGS. 3 to 13.

Transfer set holder 52b includes a driving slot 58 that slides over and secures in a rotatable manner to a peg 78b extending from an apparatus (not seen in FIG. 2) threaded onto and driven translatably by lead screw 46. Peg 78b pushes and pulls upper half 74 and lower half 76 (which lock together when lid 66 of housing 64 is closed onto lower portion 68 of housing 64) of transfer set holder 52b towards and away from, respectively, stationary port holder 52a when lead screw 46 is turned (e.g., manually or via a motor).

Slot 58 extends circumferentially around transfer set holder 52b allowing the gear train to rotate holder 52b, while or after peg 78b translates holder 58b. When peg 78b pulls transfer set holder towards gear 42, slots 54 of transfer set holder 52b come free from pegs 78a of lower portion 68 and lid 66, allowing transfer set holder 52b to be rotated.

Device gear 44 connected to transfer set holder 52b is likewise split along centerline $C_L$, creating an upper portion 44a of gear 44 connected to upper half 74 of transfer set holder 52b and a lower portion 44b of gear 44 connected to lower half 76 of transfer set holder 52b. Portions 44a and 44b operate together when upper half 74 and lower half 76 of transfer set holder 52b are positioned together (when lid 66 of housing 64 is closed onto lower portion 68 of housing 64).

When driving peg 78b pulls lower half 76 connected to upper half 74 of transfer set holder 52b fully away from stationary port holder 52a, the connectors become uncapped, and gear 44 (mated halves 44a and 44b) comes into operable engagement with gear 42 as described above. The gear train driving gear 42 can thereafter rotate transfer set holder 52b relative to port holder 52a. After being rotated, e.g., one-hundred-eighty degrees, driving peg 78b pushes transfer set holder 52b (now at half 74), such that slots 54 of transfer set holder 52b reengage with pegs 78a, and the connectors of transfer set holder 52b reengage with fixed port holder 52a.

Transfer set holder 52b holds a spike connector 80 and a male plug 86, shown in FIGS. 3 to 13. When driving peg 78b pushes transfer set holder 52b back into engagement with fixed port holder 52a, device 50 in one embodiment mates spike connector 80 (patient) connector with port connector 90 (supply connector) and male plug 86 with female plug 96 shown below in FIGS. 3 to 13. When the supply bag connected to connector 90 is emptied, transfer set holder is again moved away from port holder 82a. Holder 52b is translated so that the rotational gears mesh, the gear train rotates holder 52b again one-hundred-eight degrees, and holder 52b is pushed back to holder 52a, putting the caps back onto the connectors. As discussed below, during rotation of device 50, light applicator sterilizes the connectors.

An optional slide holder 52c in one embodiment holds male plug 86 (transfer set holder 52b holds spike connector 80). Slide holder 52c slides back and forth relative to transfer set holder 52b and port holder 52a and provides an additional degree of movement freedom if needed, as shown below. It should be noted that the drive train of FIG. 1 is for when slide holder 52c is not provided. If slide holder 52c is provided, it can be driven via a driving peg 78b as discussed above of transfer set holder 52b.

FIGS. 3 to 6 illustrates the disconnection/reconnection sequence from above, e.g., with lid 66 has removed to aid illustration. Lower portion 68 of housing is seen however. FIG. 3 shows an embodiment of device 50 in a state in which both connectors 80 and 90 are secured at their connecting ends to a mating plug 96 and 86, respectively. FIG. 4 shows that transfer set holder 52b is slid away from port holder 52a, e.g., from the position shown in FIG. 3, which pulls a spike 84 of patient connector 80 out of female plug 96 and pulls male plug 86 away from port connector 90. In an alternative embodiment, slide holder 52c holding plug 86 is provided and is also translated away from port connector 52a for additional clearance, which can be seen by the relative difference in distance of the connection end of plug 86 and spike 84 between FIGS. 3 and 4.

In FIG. 5, transfer set holder 52b is rotated relative to the light applicator housing such that plug 86 is now aligned with plug 96 and patient connector 80 is aligned with port connector 90. At this point in the process, a light activator 70 (located above and below spike 84 of patient connector 80 in one embodiment but alternatively additionally above and below supply connector 90) in lid 66 and lower portion 68 of housing 64 is energized to irradiate any one, or more, or all of the exposed surfaces, namely spike 84 of connector 80, diaphragm 94 of connector 90 if still connected to the connector, inner surfaces of connector 80 and 90, inner and outer surfaces of plugs 86 and 96 and any other needed surface of connectors 80 and 90 and plugs 86 and 96. Light applicator 70 can be energized manually or automatically. As discussed in the incorporated patents and application, the irradiation can last for approximately a minute, for example, or be controlled by measuring energy imparted to the connectors.

In FIG. 6, transfer set holder 52b is translated toward port holder 52a, such that plugs 86 and 96 are mated and spike connector 84 of patient connector 80 spikes through diaphragm 94 of port connector 90 to enable fluid from a supply bag to flow (directly or via a disposable cassette) through connector 90, connector 80, the patient's transfer set, the patient's indwelling catheter and into the patient's peritoneum. A like connection is made to enable fluid to flow from the patient's peritoneum through patient connector 80, a drain connector similar to supply connector 90, which carries the spent fluid to a drain or drain bag. Although not illustrated expressly in FIG. 6, slide holder 52c holding plug 86 is translated again automatically to connect plug 86 to plug 96, which can be seen for example by the difference in relative positioning of plug 86 and the box representing transfer set holder 52b between FIGS. 5 and 6.

To disconnect the patient connector 80 from supply connector 90, the steps shown in FIGS. 3 to 6 are performed in reverse, here, from FIG. 6 to FIG. 3. UV applicator 70 is again energized in reverse FIG. 5, the second step in disconnection, after connector 80 is removed from connector 90 and plug 86 is removed from plug 96. In this manner, the connectors and plugs are again disinfected before disconnection is completed via rotation in reverse FIG. 4 and reconnection of the connectors to the respective plugs in reverse FIG. 3.

Referring now to FIGS. 7 to 13, the disconnection sequence just described is shown schematically. It should be appreciated that the connection sequence just shown in FIGS. 3 to 6 is also illustrated by FIGS. 7 to 13, only the sequence in FIGS. 7 to 13 occur in reverse. The reason for two additional figures is that the separate translations of slide holder 52c to transfer set holder 52b and of transfer set holder 52b relatively to port holder 52a are broken out here in separate steps in FIGS. 8 and 9 and FIGS. 11 and 12.

FIGS. 7 to 13 also illustrate the use of a valve 60 to open and close supply line 92. Valve 60 can be opened and closed automatically, e.g., via automatically actuated occluder halves 22 and 24 shown and described above. Alternatively, valve 60 is operated manually. In FIGS. 7 to 13, valve 60 is shown as being part port holder 52a. It is contemplated to provide valve 60 as a manually or automatically actuated valve within port holder 52a. Alternatively, valve 60 can be a line clamp on supply line 92. Further alternatively, valve 60 is integrated with an APD cycler, which closes and opens supply line 92 automatically. In FIG. 1, valve 60 is formed via occluder halves 22 and 24 and is located on occluder subassembly 20 of system 10.

In FIG. 7, valve 60 is closed such that fluid cannot flow from supply line 92 to patient line 82 or flow from the patient through patient line 82, to a drain line. Patient connector 80 is connected sealingly to port connector 90. Slide holder 52c is fully advanced towards port holder 52a and thus plug 86 carried by slide holder 52c is mated with plug 96 held by port holder 52a.

In FIG. 8, clamp 60 remains closed. A motor (not illustrated) drives a slide holder actuator 62, in a manner similar above for transfer set holder 52b, to pull slide holder 52c and port 86 held by slide holder 82c away from port holder 52a. This action causes plug 86 to disconnect from plug 96 held by port holder 52a. Alternatively, slide holder 52c is not used and this step is skipped.

In FIG. 9, valve 60 remains closed. Here, the transfer set holder 52b is pulled translationally away from port holder 52a. This action pulls plugs 86 and 96 apart further. Moreover, the action causes spike 84 of patient connector 80 to become disconnected from port connector 90.

In FIG. 10, valve 60 remains closed and transfer set holder 52b is rotated one-hundred-eighty degrees relative to port holder 52a, so that plug 86 and slide holder 52c are now aligned with port connector 90, while patient connector 80 is aligned with plug 96. In this step, UV applicator 70 provides sufficient energy over time to effectively disinfect pertinent portions of the connectors and plugs, such as the spike and sealing area of patient connector 80, the sealing area of port connector 90, and the sealing areas of plugs 86 and 96.

FIG. 11 illustrates a first translational motion in the reconnection of transfer set holder 52b to port holder 52a. Here, the entire transfer set holder 52b is translated inward towards port holder 52a. Valve 60 remains closed. This action causes spike 84 and sealing area of patient connector 80 to mate with the sealing area of plug 96.

In FIG. 12 valve 60 remains closed, a motor translates actuator 62, slide holder 52c and plug 86 carried by slide holder 52c relative to transfer set holder 52b and port holder 52a such that plug 86 mates with and seals to port connector 90. In FIG. 13, valve 60 is opened allowing any fluid trapped upstream of the valve to flow to drain from the system or to allow new fresh solution to be delivered via supply line 92.

Upon reconnecting connectors 80 and 90, a first step as in FIG. 7 is to close valve 60. In reconnection, after the transfer set holder is rotated, the UV flash 70 is energized, and reconnection of the connectors takes place, valve 60 is opened, like in FIG. 13, to allow fluid to flow through the connectors.

Referring now to FIG. 14, a temporary transfer set disconnect/reconnect feature is illustrated. Connection/disconnection device 50 allows patient connector 80 and plug 96 to be removed together from transfer set holder 52b and port holder 52a, respectively, e.g., by rotating lid 64 from lower portion 66 of housing 62, thereby rotating upper portion 74 of drum device 10 from lower portion 76 of device 50, exposing connected patient connector 80 and plug 96. The patient may do this for a number of reasons, for example, to halt therapy for a time so that the patient can conduct other business, e.g., to go to the bathroom, before returning to reinitiate therapy.

When the patient returns, the patient opens lid 64 from lower portion 66 of housing 62, thereby rotating upper portion 74 of drum device 50 from lower portion 76 of device 50, exposing the holding portions of lower portion 76 of device 50. The patient reinserts patient connector 80 and plug 96 into transfer set holder 52b and port holder 52a, respectively, and closes lid 62 to allow treatment to proceed.

Afterwards, clamp or valve 60 is closed. Next, transfer set holder 52b and slide holder 52c are translated away from port holder 52a to disconnect patient connector 80 from plug 96 and plug 86 from port connector 90. Next, transfer set holder 52b is rotated, such that patient connector 80 is aligned with port connector 90. UV applicator 70 irradiates the connectors and plugs to disinfect these components. Next, transfer set holder 52b and slide holder 52c are translated towards port connector 52a, connecting connector 80 to connector 90 and mating plugs 86 and 96. Valve or clamp 60 is then opened to allow dialysis fluid flow through the system.

Connector Improvements

Figure 16:
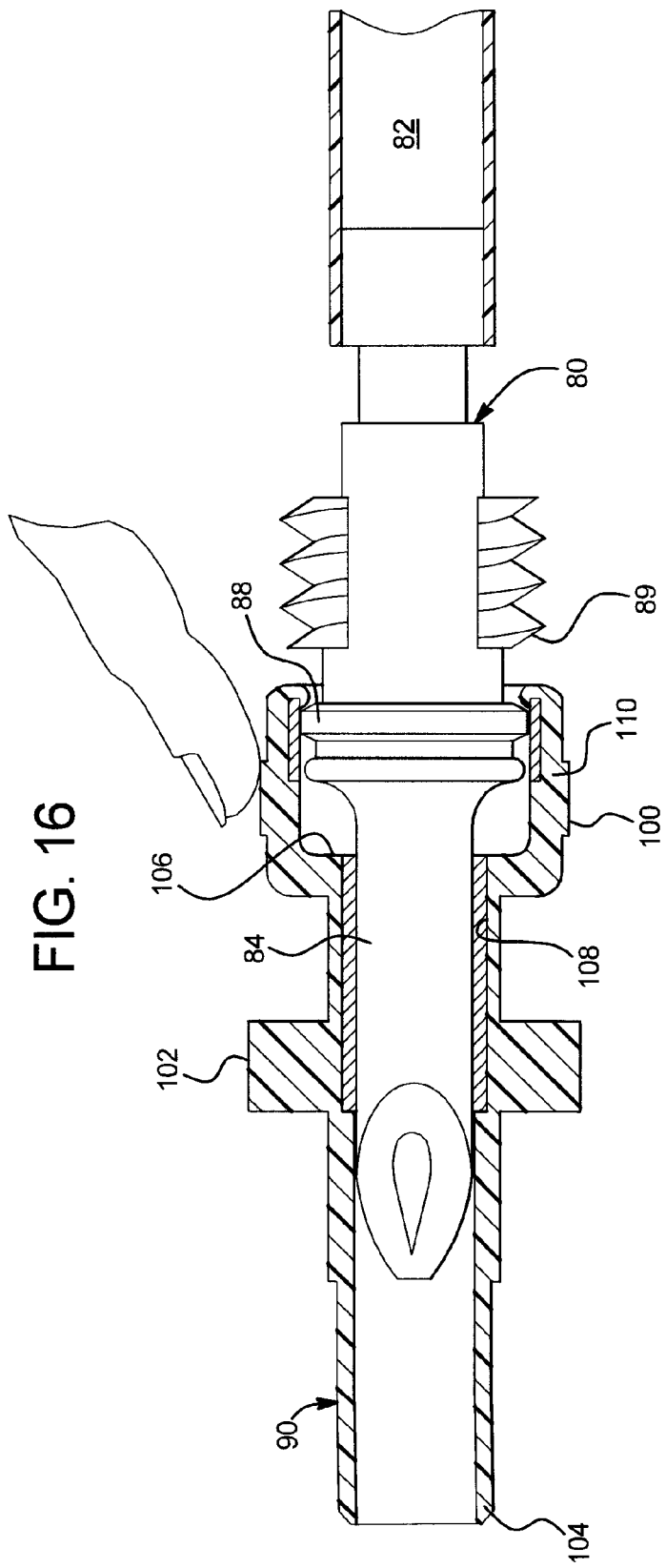

Referring now to FIGS. 15 to 17, an embodiment for supply or port connector 90 is illustrated. Port connector 90 is made of a suitable medical grade material, such as polyvinylchloride ("PVC") or polypropylene ("PP"). Port connector 90 includes a tube holding or tube sealing portion 104, a flange portion 102 and a shroud portion 100. Tube portion 104 is sized to fit snuggly within a tube, which can be semi-permanently or permanently fixed to tube portion 104. As discussed below in connection with FIGS. 20 and 21, tube connecting portion 104 in an embodiment includes one or more barbed ring (not illustrated here). Flange portion 102 is sized to fit within port connector 52a of connection/disconnection device 50 as illustrated below in connection with FIG. 19.

As seen in FIG. 15, shroud 100 is sized and shaped so as to prevent a person's finger from contacting a radially extending wall 106 at the base of shroud 100 and from contacting an inner, annular surface 108 of port connector 90. Radial wall 106 and inner annular surface 108 are primary areas of concern for contamination. These areas contact the spike 84 of patient connector 80 as seen in FIGS. 16 and 17. Preventing a person from touching radial wall 106 and inner annular surface 108 prevents those areas from becoming infected in the first place (e.g., upon temporary removal from device 50) and accordingly reduces the bacterial load on UV applicator 70 described above.

Shroud 100 includes a cylindrical wall 110, which extends longitudinally away from radial wall 106 a distance sufficient to ensure that the patient's finger does not touch radial wall 106 or inner annular surface 108. An inner diameter of cylindrical wall 110 is sized to seal to or press-fit to a sealing portion 88 of patient connector 80. This is a secondary seal to a primary seal made between spike 84 and inner wall 108 of connector 90.

As seen in FIG. 16, wall 110 protects sealing portion 88 and an inner surface of wall 110 close to the edge of the wall, while patient connector 80 is connected to supply connector 90. Also, wall 110 prevents secondary sealing portion 88 from touching and potentially transmitting contamination to radial wall 106 of port connector 90. Further, UV applicator 70 can irradiate and destroy any contamination that does appear on sealing portion 88.

Figure 19:
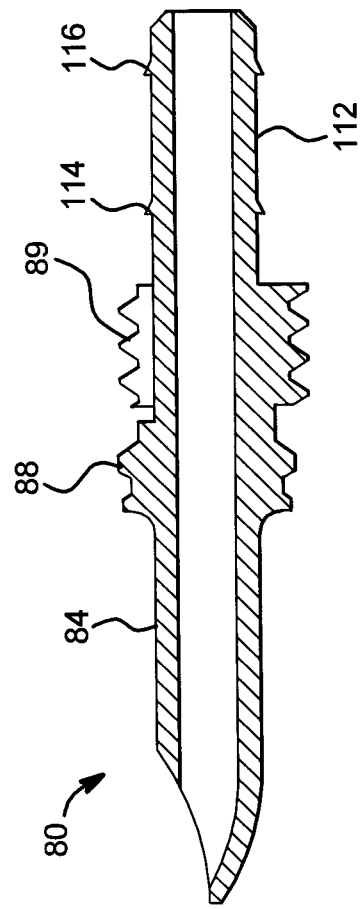

Referring now to FIG. 19, an additional benefit of port connector 90 is illustrated. Connector 90 is shown mounted in port holder portion 52a of connection/disconnection device 50 or other port holder. Here, flange 102 of port connector 90 is spaced apart from shroud 100 a distance sufficient to enable shroud 100 to reside past the edge of port holder 52a or other port holder. When port connector 90 is loaded initially into port holder 52a (or other port holder), the mating end of connector 90 is protected via a tip protector 120. The configuration of connector 90 and port holder 52a (or other port holder) enables connector 90 with tip protector 120 attached to be loaded into port holder 52a (or other port holder) before having to remove tip protector 120. This enables the patient once connector 90 is loaded into port holder 52a (or other port holder) to grasp connection device 50 (or other connection device) to remove tip protector 120 as opposed to holding connector 90 directly to remove the tip protector. This feature further isolates connector 90 from human touch and further lessens the likelihood that connector 90 will become contaminated in the first place.

Figure 18:
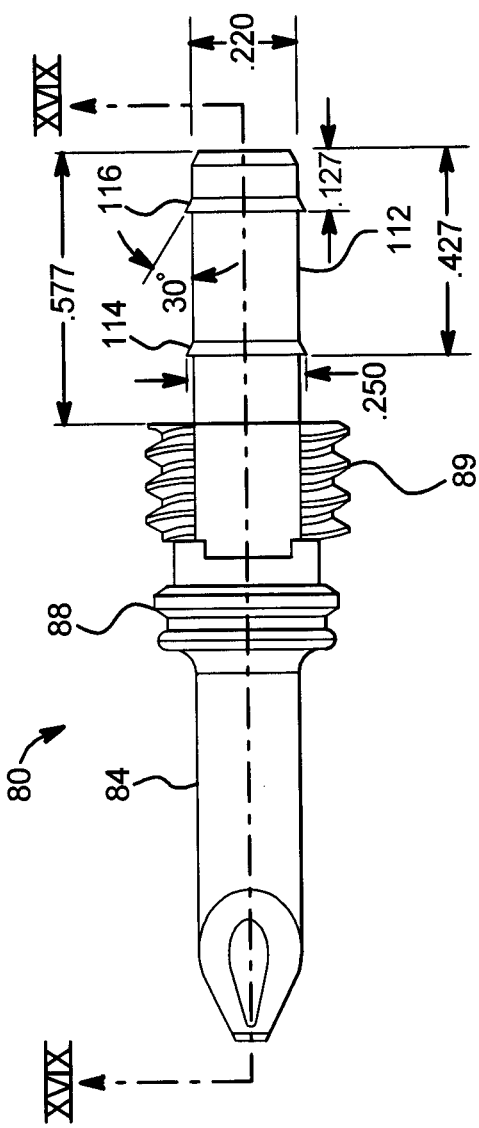
FIGS. 18 and 19 are top and side sectioned views, respectively, of an improved connector with a plurality of barbed sealing bands or rings.

Referring now to FIGS. 18 and 19, an embodiment for patient connector or male connector 80 is illustrated. FIG. 19 shows a section of connector 80 taken along line XVIX-XVIX of FIG. 18. Patient connector 80 can be made of any of the materials discussed above for supply connector 90. For reference, patient connector 80 includes a spike tip 84, a sealing area 88, a flange portion 89, which in the illustrated embodiment is threaded. The threaded flange portion 89 threads onto a mating portion of an overall transfer set assembly, which is sometimes referred to as a flow control barrel.

The patient connector 80 also includes a tube sealing area 112, which receives patient tube 82 described above in connection with FIGS. 16 to 18.

In the illustrated embodiment, sealing portion 112 includes a plurality of barbed rings or projections 114 and 116. Barbed rings 114 and 116 include a surface angled so that a length of tube 82 can slide over tube sealing portion 112 relatively easily. In an embodiment, the angle of the surface is about thirty degrees although other angles could be used. Thirty degrees offers enough barb height for bite into mating tube 82 without the barb becoming too long. Thirty degrees also facilitates easy assembly.

In the illustrated embodiment, barbed rings 114 and 116 are spaced apart about 0.3 inch (7.62 mm) The outer diameter of barbed ring is 0.250 inch (6.35 mm), extending from the surface of sealing portion 112, which has an outer diameter of 0.220 inch (5.59 mm)

Threaded flange portion is spaced apart from the end of sealing area 112 a distance of 0.577 in (14.7 mm) in one implementation. Thus, barbed rings 114 and 116 in one embodiment are spaced apart by a distance at least as large as the inner diameter of sealing portion 112. The length of sealing portion 112 is at least two times the outer diameter of sealing portion 112 in the illustrated embodiment. Further, if tube 82 attached to connector 80 has an outer diameter of 0.250 inch (6.35 mm), then the height of the barb off of the surface of portion 112 can be less than or equal to a thickness of tube 82. These dimensions help secure a proper and easily made seal between connector 80 and tube 82.

While barbed rings 114 and 116 enable tube 82 to be positioned over sealing section 112 relatively easily, the barbed rings provide a tube removal force greater than a desired 5 lbs. In tests performed on a spike connector 80 having barbed rings 114 and 116, a mean pull of force of 10.6 lbs was measured, with a standard deviation of 0.2 lbs. Thus, even after remaining three times the standard deviation less the mean pull force of 10.6 lbs, the measured pull-off force is greater than the 5 lbs desired pull-off force.

Figure 20:
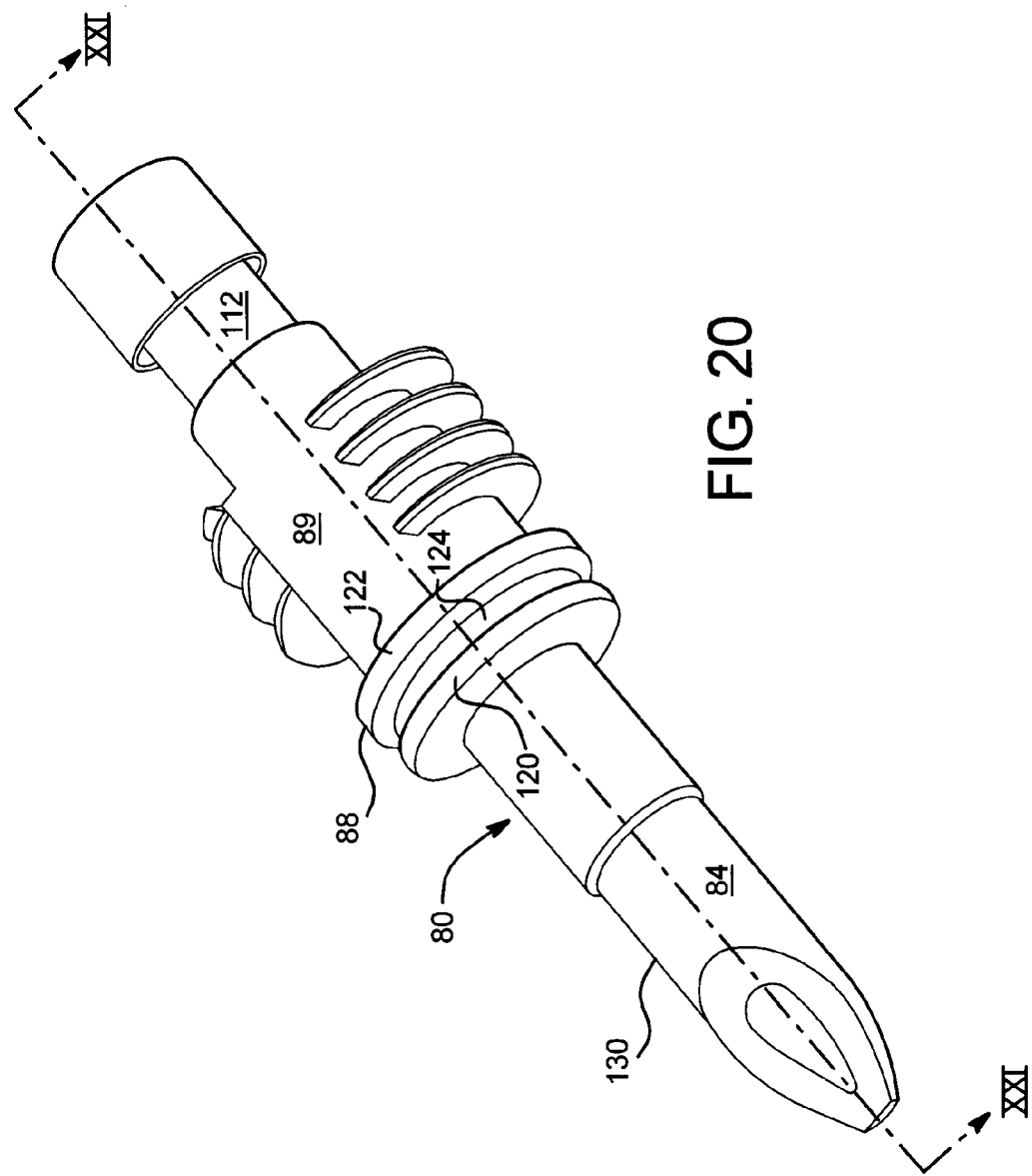
FIGS. 20 and 21 are perspective and sectional views of a spike connector having a stepped-down spike end diameter and a spike to port connector snap-fitted connection, respectively.
Figure 21:
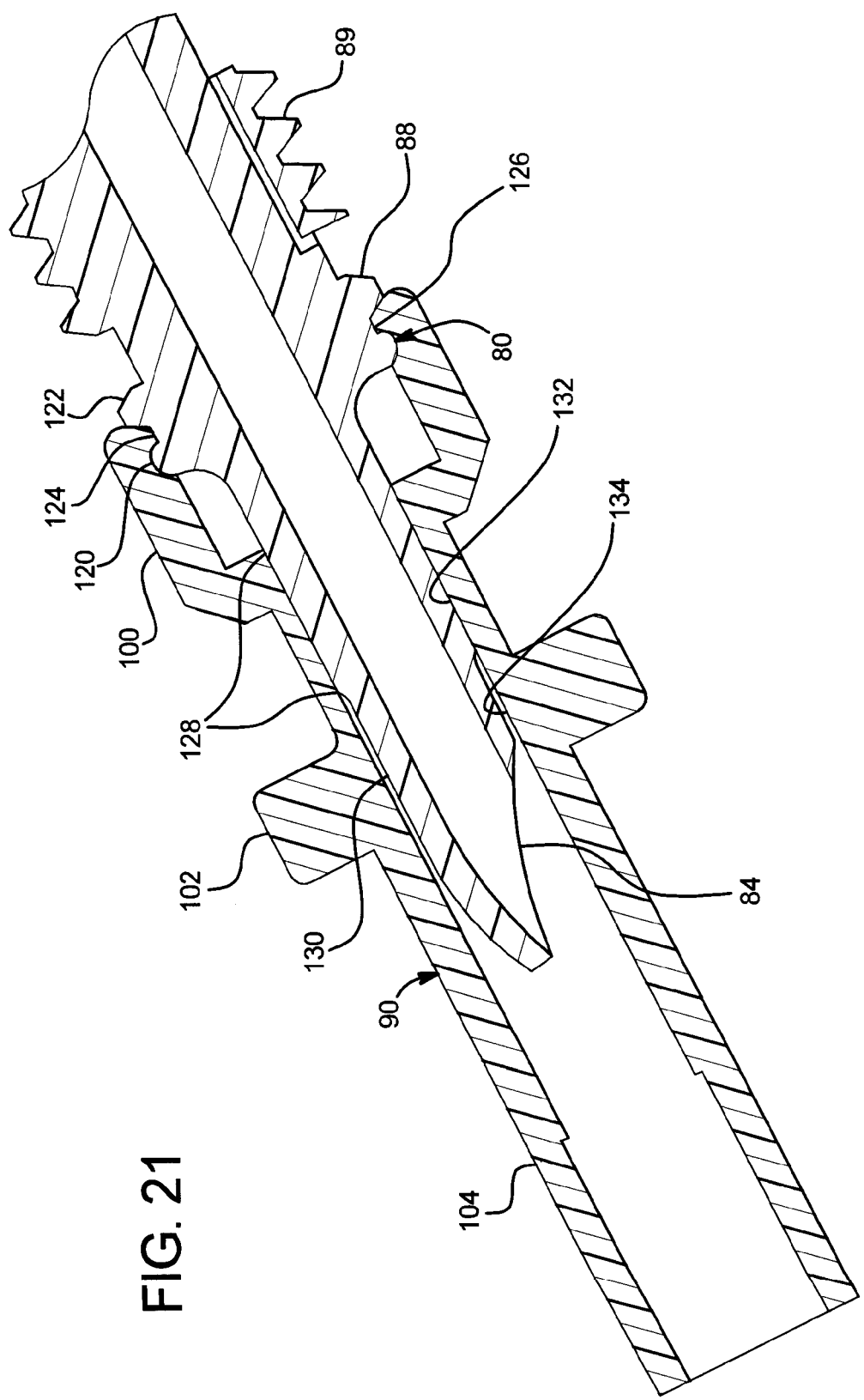

Referring now to FIGS. 20 and 21 (FIG. 21 is a sectioned view of connector 80 taken along line XXI-XXI of FIG. 20, and which shows mated port connector 90 in cross-section), another embodiment for patient connector or male connector 80 and port connector 90 is illustrated. Each of the teachings in connection with FIGS. 15 to 21 is applicable also to the embodiments of FIGS. 20 and 21 and vice versa. In FIGS. 20 and 21, sealing portion 88 of spike connector 80 includes outwardly extending rings 120 and 122, which define in between an annular groove 124. Shroud or port 100 of connector 90 defines or includes an undercut geometry or inwardly extending projection 126, which snap-fits or frictionally fits into annular groove 124 of connector 80. In an alternative embodiment, shroud or port 100 of connector 90 defines an annular groove, while sealing portion 88 of connector 80 includes or defines an outwardly projecting ring that snap-fits or frictionally fits into the alternative annular groove shroud or port 100.

The snap-fitting or frictional relationship just described enables spike connector 80 to have a frictional engaging portion 128 and a stepped-down portion 130. Frictional engaging portion 128 engages an inner annular surface portion 132 of port connector 90. Stepped-down portion 128 of spike 84 produces an inner, annular surface portion 134 of connector 90 at which spike 84 does not contact the connector 90. Reducing the contact area of spike 84 with inner, annular surface portion 132 of connector 90 reduces the overall connection and disconnection force required to insert spike connector 80 into port connector 90.

Also, because the connector set of FIGS. 20 and 21 does not require all of spike 84 to seal to the inner annular surface of connector 90, the geometry of the tip portion of spike 84 can be optimized to suit other performance characteristics, such as desired connection and disconnection force as provided here via stepped-down portion 130 of spike 84 or a puncturing optimization of spike 84, for example.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A peritoneal dialysis connector set comprising:
a male connector including
 a spike portion having a distal end and a proximal end,
 a spike located at the distal end,
 a seal apparatus located at the proximal end and fixed to the spike portion, the seal apparatus including an outer surface, and
 a first tube connection portion adjacent to the spike portion; and
a female connector including
 a second tube connection portion having a tube section and a mouth section, the tube section having a tube end configured to receive a tube, the mouth section having a mouth end configured to receive the spike, the second tube connection portion defining a lumen extending longitudinally between the tube end and the mouth end, and
 a shroud including a radial wall and an axial wall, the radial wall extending from the mouth end in a radial direction and the axial wall including an inner surface and extending from the radial wall in an axial direction so as to protect the mouth end from human touch, the radial wall and the axial wall forming an enclosure sized (i) to seal to the seal apparatus of the male connector via the outer surface of the seal apparatus contacting the inner surface of the axial wall of the shroud and (ii) to enable the seal apparatus to remain safely away from the mouth end when the male connector and female connector are mated.

2. The peritoneal dialysis connector set of claim 1, wherein at least one of the spike portion, the first tube connection portion, the second tube connection portion and the shroud are cylindrical.

3. The peritoneal dialysis connector set of claim 2, wherein the shroud of the female connector has a larger diameter than a diameter of the second tube connection portion of the female connector.

4. The peritoneal dialysis connector set of claim 1, wherein one of the first and second tube connection portions is a male port sized to fit sealingly inside a tube.

5. The peritoneal dialysis connector set of claim 1, wherein the male and female connectors are configured to snap-fit together.

6. The peritoneal dialysis connector set of claim 1, wherein the female connector includes a flange, the flange sized and positioned to enable the female connector to be held by a fixture when the male connector is inserted into the female connector.

7. The peritoneal dialysis connector set of claim 6, wherein the shroud is spaced away from the flange a distance sufficient to enable the shroud to extend past an end of the fixture when held by the fixture.

8. The peritoneal dialysis connector set of claim 1, wherein at least one of the male and female connectors is provided initially with a tip protector.

9. The peritoneal dialysis connector set of claim 1, wherein at least one of the male and female connectors is made of a material that can be irradiated for sterilization.

10. The peritoneal dialysis connector set of claim 1, wherein the female connector includes a pierceable diaphragm attached to an end of the shroud.

11. The peritoneal dialysis connector set of claim 1, wherein at least one of the first and second tube connection portions includes at least one barb for sealing to a tube.

12. A peritoneal dialysis connector set comprising:
a male connector including a sealing portion and a spike connector including a spike, the sealing portion fixed to the spike connector and including an outer surface; and
a female connector including
 a tube connection portion having a tube section and a mouth section, the tube section having a tube end configured to receive a tube, the mouth section having a mouth end configured to receive the spike connector, the tube connection portion defining a lumen extending longitudinally between the tube end and the mouth end, and
 a shroud including a radial wall and an axial wall, the radial wall extending from the mouth end in a radial direction and the axial wall including an inner surface and extending from the radial wall in an axial direction so as to protect the mouth end of the tube connection portion from human touch, the axial wall of the shroud sealing to the sealing portion of the male connector via the outer surface of the sealing portion contacting the inner surface of the axial wall of the shroud, the axial wall extending axially from the radial wall a distance sufficient to preclude the sealing portion of the male connector from contacting the mouth end of the tube connection portion of the female connector.

13. The peritoneal dialysis connector set of claim 12, wherein at least one of the sealing portion, the tube connection portion, and the shroud are cylindrical.

14. The peritoneal dialysis connector set of claim 12, wherein the male connector includes at least one barb for sealing to a tube.

15. The peritoneal dialysis connector set of claim 12, wherein the female connector includes a flange, the shroud spaced away from the flange a distance sufficient to enable a fixture to fit between the shroud and the flange, so that the fixture can hold the female connector.

16. The peritoneal dialysis connector set of claim 12, wherein the male and female connectors are configured to snap-fit together.

17. A peritoneal dialysis connector comprising:
a body including a first end and a second end, the second end of the body having an outer diameter;
a spike located at the first end of the body;
a sealing ring located adjacent to the spike, the sealing ring sized to seal inside a female connector;
threads located adjacent to the sealing ring; and
first and second barbed rings located adjacent to the threads at the second end of the body, the first and second barbed rings spaced apart a distance at least as large as the outer diameter of the body and configured to seal the second end of the body to a tube having a thickness, and wherein (i) a length of the second end of the body extending from an edge of the second end to the threads is at least two times that of the outer diameter of the second end of the body, and (ii) the first and second barbed rings extend radially away from the body a distance that is less than or equal to the thickness of the tube.

18. The peritoneal dialysis connector of claim 17, wherein the outer diameter of the second end of the body is about 0.25 inch.

19. The peritoneal dialysis connector of claim 17, wherein the first and second barbed rings are sized and configured to provide a resistive force of at least five pounds that a person must overcome to remove the tube from the second end of the body.

20. The peritoneal dialysis connector of claim 17, wherein the first and second barbed rings include a tapered surface extending at an angle of about thirty degrees.

21. The peritoneal dialysis connector of claim 17, wherein the first and second barbed rings are formed integrally with the body.

22. The peritoneal dialysis connector of claim 17, wherein the outer diameter of the second end of the body is 0.22 inch.

23. The peritoneal dialysis connector of claim 17, wherein the second end of the body is cylindrical.

24. A peritoneal dialysis connector set comprising:
a port connector including
a tube connection portion having a tube section and a mouth section, and
a port; and
a spike connector including (i) a spike portion including a spike and (ii) a sealing portion located adjacent to the spike portion, the sealing portion fixed to the spike connector and including an outer surface, the sealing portion configured to snap-fit to the port of the port connector,
wherein the tube connection portion defines a lumen extending longitudinally between a tube end of the tube section and a mouth end of the mouth section, the tube end configured to receive a tube and the mouth end configured to receive the spike portion, and wherein the port includes a radial wall and an axial wall, the radial wall extending from the mouth end in a radial direction and the axial wall including an inner surface and extending from the radial wall in an axial direction so as to protect the mouth end from human touch, the axial wall of the port sealing to the sealing portion of the spike connector via the outer surface of the sealing portion contacting the inner surface of the axial wall.

25. The peritoneal dialysis connector set of claim 24, wherein the port includes an inwardly projecting ring that snap-fits into a groove in the sealing portion of the spike connector.

26. The peritoneal dialysis connector set of claim 24, wherein the sealing portion of the spike connector includes an outwardly projecting ring that snap-fits into a groove in an inner surface of a wall of the port.

27. The peritoneal dialysis connector set of claim 24, the port including an undercut feature sized to snap-fit to an annular groove of the sealing portion of the spike connector.

28. The peritoneal dialysis connector set of claim 27, wherein the annular groove of the spike connector is formed between two annular rings projecting from a body of the spike connector.

29. The peritoneal dialysis connector set of claim 24, wherein the spike connector includes a tube connection portion located adjacent to the spike portion.

30. The peritoneal dialysis connector set of claim 24, wherein the port includes a cylindrical wall configured to fit over the sealing portion of the spike connector.

31. The peritoneal dialysis connector set of claim 24, wherein the snap-fit configuration is structured so as to provide a resistance that can be overcome manually or via a connection/disconnection device.

* * * * *